US008609359B2

(12) United States Patent
Hasan et al.

(10) Patent No.: US 8,609,359 B2
(45) Date of Patent: Dec. 17, 2013

(54) METHODS FOR DETERMINING THE CONCENTRATION OF GAMMA-HYDROXY BUTYRIC ACID (GHB) IN A SAMPLE

(75) Inventors: Lara Hasan, Allschwill (CH);
Michel-Angelo Sciotti, Frick (CH);
Thomas Jermann, Röschenz (CH);
Jakob Matthias Weber, Reinach (CH);
Daniel Gygax, Himmelried (CH);
André Scholer, Bottmingen (CH)

(73) Assignee: Bühlmann Laboratories AG, Schönenbuch (CH)

( * ) Notice: Subject to any disclaimer, the term of this patent is extended or adjusted under 35 U.S.C. 154(b) by 0 days.

(21) Appl. No.: 13/318,054

(22) PCT Filed: Apr. 23, 2010

(86) PCT No.: PCT/EP2010/055436
§ 371 (c)(1),
(2), (4) Date: Oct. 28, 2011

(87) PCT Pub. No.: WO2010/124999
PCT Pub. Date: Nov. 4, 2010

(65) Prior Publication Data
US 2012/0052520 A1    Mar. 1, 2012

(30) Foreign Application Priority Data

Apr. 28, 2009 (EP) ..................... 09005884

(51) Int. Cl.
*C12Q 1/26* (2006.01)
(52) U.S. Cl.
USPC ......................................................... 435/25
(58) Field of Classification Search
USPC ......................................................... 435/25
See application file for complete search history.

(56) References Cited

U.S. PATENT DOCUMENTS

| | | | |
|---|---|---|---|
| 6,153,147 A | 11/2000 | Craig | |
| 6,617,123 B1 * | 9/2003 | Smith | 435/19 |
| 6,703,216 B2 | 3/2004 | Parsons et al. | |
| 2001/0046710 A1 | 11/2001 | Cutler | |
| 2003/0175846 A1 * | 9/2003 | Parsons et al. | 435/25 |
| 2005/0233459 A1 | 10/2005 | Melker et al. | |

OTHER PUBLICATIONS

Bravo D. et al. Reliable, Sensitive, Rapid and Quantitative Enzyme Based Assay for Gamma Hydroxybutyric Acid. J Forensic Sciences Mar. 2004 49(2)379-387, legible copy provided.*
Hasan L. et al. An Enzymatic Method to Determine GHB in Serum and Urine. Therapeutic Drug Monitoring Dec. 2011 33(6)757-765.*
Kaufman E. et al. Purification and Characterization of an NADP+ Linked Alcohol Oxido-Reductase . . . J of Neurochemistry 32:699-712, 1979.*

Baldacci, A. et al., "Determination of y-hydroxybutyric acid in human urine by capillary electrophoresis with indirect UV detection and confirmation with electrospray ionization ion-trap mass spectrometry," Journal of Chromatography A, 990 (2003) 99-110.
Blanchet, B. et al., "Capillary gas chromatographic deterination of 1,4-butanediol and y-hydroxybutyrate in human plasma and urine," Journal of Chromatography B, 769 (2002) 221-226.
Bravo, D. T. et al,. "Reliable, Sensitive, Rapid and Quantitative Enzyme-Based Assay for Gamma-Hydroxybutyric Acid (GHB)*", J. Forensic Sci., Mar. 2004, vol. 49, No. 2, 379-387.
Capehart, M., "A condom for your drink," Online Archives for the Las Vegas CityLife, Jun. 13, 2002, 2 pp.
Elian, A. A., "A novel method for GHB detection in urine and its application in drug-facilitated sexual assaults," Forensic Science International 109 (2000) 183-187.
Ferrara, S. D. et al., "Therapeutic gamma-hydroxybutyric acid monitoring in plasma and urine by gas chromatography-mass spectrometry," Journal of Pharmaceutical & Biomedical Analysis, vol. 11, No. 6, 1993, 483-487.
Jordi, M., "Determination of formic acid, glycolate, gamma-hydroxybutyrate together with other endogenous orgabnic acids in human serum an urine," Diploma Workat the Technical High School of both Basel, Switzerland, Department Industry, Chemistry, Muttenz, 2003.
Jordi, M. et al., "GHB Determination With Ion Chromatography," Poster at the IATDMCT Congress 2003, Basel Switzerland.
Kankaanpaa, A. et al., "Determination of y-hydroxybutyrate (GHB) and its precursors in blood and urine samples: A salting-out approach," Forensic Science International 170 (2007) 133-138.
Kaufman, E. E. et al "An Overview of y-Hydroxybutyrate Catabolism; The Role of the Cytosolic NADP+– Dependent Oxidoreductase EC 1.1.1.19 and of a Mitochondrial Hydroxyacid-Oxoacid Transhydrogenase in the Initial, Rate-Limiting Step in This Pathway," Neurochemical Research, vol. 16, No. 9, 1991, 965-974.
Kintz, P. et al., "Testing for GHB in Hair by GC/MS/MS after a Single Exposure. Application to document Sexual Assault," J. Forensic Sci, Jan. 2003, vol. 48, No. 1, 195-200.
Liu, W. et al., "Detection of y-Hydroxybutyrate (GHB) in Beverages," Journal of Forensic Medicine, Apr. 2007, vol. 23, No. 2, 120-122 and 129 (with English Abstract).
McCusker, R. R. et al., "Analysis of Gamma-Hydroxybutyrate (GHB) in Urine by Gas Chromatography-Mass Spectrometry," Journal of Analytical Toxicology, vol. 23, Sep. 1999, 301-305.
Paul, R. et al., "GC-MS-MS Determination of Gamma-Hydroxybutyrate in Blood and Urine," Journal of Analytical Toxicology, vol. 30, Jul./Aug. 2006, 375-379.
Shen, M. et al., "Study on Appraisement and Determination GHB Levels in Hair," Journal of Forensic Medicine, Feb. 2006, vol. 22, No. 1, 48-51 (with English Abstract).
Villain, M. et al., "Ultra-rapid procedure to test for y-hydroxybutyric acid in blood and urine by gas chromatography-mass spectrometry," Journal of Chromatography B, 792 (2003) 83-87.
Zhang, S-Y et al., "A Color Test for Rapid Screening of Gamma-hydroxybutyric Acid (GHB) and Gamma-butyrolactone (GBL) in Drink and Urine," Journal of Forensic Medicine, Dec. 2006, vol. 22, No. 6, 424-427 (with English Abstract).

* cited by examiner

*Primary Examiner* — Ralph Gitomer
(74) *Attorney, Agent, or Firm* — RatnerPrestia

(57) ABSTRACT

Methods to determine the concentration of gamma-hydroxy butyric acid (GHB) in a sample as well as compositions and a kit suitable for carrying out said methods. Also, the use of the methods for application on a microtiter plate or an auto-analyzer.

17 Claims, 12 Drawing Sheets

Fig. 3

Assay 1

Reagents   Ra (pH 9.0):
Tris-HCl   750 mM
OxA   33.75 mM
EDTA   6.75 mM

Rb:   NAD⁺   6.75 mM

Rc:   GHBDH   132 µg/ml

Procedure

Step 1: 220 µl Ra:Rb:Rc (1 vol:1 vol:1 vol)

Step 2: 8 µl Sample / Cal + 22 µl H$_2$O

→ Incubate 8 min at 37 °C

→ Read from 2nd to 8th min (340 nm)

Assay 2

Reagents   Ra' (pH 9.0):
Tris-HCl   420 mM
OxA   15 mM
EDTA   3 mM

Rb' (pH 7.0):
NAD⁺   9 mM
GHBDH   200 µg/ml

Procedure

Step 1: 220 µl Ra':Rb'   (3 vol:1 vol)

Step 2: 8 µl Sample / Cal + 22 µl H$_2$O

→ Incubate 8 min at 37 °C

→ Read from 2nd to 8th min (340 nm)

Fig. 4

Reagents

R1a (pH 10.0):
- AMPD 500 mM
- OxA 20 mM
- EDTA 4 mM

R1b: NAD$^+$ 12 mM

R2: GHBDH 0.3 mg/ml

Cal GHB 100 and 1000 µM

Con L 150 and H 800 µM

Procedure

Step 1: 165 µl R1a:R1b (3 vol: 1 vol)

Step 2: 8 µl Sample / Cal + 30 µl H2O

→ Incubate 2 min at 37 °C

Step 3: 35 µl R2 + 12 µl H$_2$O

→ Incubate 6 min at 37 °C

→ Read from 2nd to 8th min (340 nm)

Fig. 6

| Urine samples spiked with GHB | GHB (µM) Observed (O) | Expected (E) | Spiking Recoveries O/E (%) |
|---|---|---|---|
| U BL1 + 0    | 15   |      |     |
| U BL1 + 100  | 115  | 115  | 100 |
| U BL1 + 500  | 495  | 515  | 96  |
| U BL1 + 1000 | 934  | 1015 | 92  |
| U BL2 + 0    | 0    |      |     |
| U BL2 + 100  | 95   | 100  | 95  |
| U BL2 + 500  | 553  | 500  | 111 |
| U BL2 + 1000 | 1070 | 1000 | 107 |
| U BL10 + 0   | 14   |      |     |
| U BL10 + 100 | 113  | 114  | 99  |
| U BL10 + 500 | 447  | 514  | 87  |
| U BL10 + 1000| 862  | 1014 | 85  |
| U GM190808 + 0    | 55   |      |    |
| U GM190808 + 100  | 152  | 155  | 98 |
| U GM190808 + 500  | 534  | 555  | 96 |
| U GM190808 + 1000 | 1005 | 1055 | 95 |
| U BL11 + 0    | 71  |      |    |
| U BL11 + 100  | 156 | 171  | 91 |
| U BL11 + 500  | 521 | 571  | 91 |
| U BL11 + 1000 | 972 | 1071 | 91 |

Fig. 7

| Serum samples spiked with GHB | ΔOD | GHB (µM) Observed (O) | GHB (µM) Expected (E) | Spiking Recoveries O/E (%) |
|---|---|---|---|---|
| S 15 + 0 | 0.000 | 0 | | |
| S 15 + 150 | 0.029 | 165 | 150 | 110 |
| S 15 + 800 | 0.141 | 833 | 800 | 104 |
| S 16 + 0 | 0.000 | 0 | | |
| S 16 + 150 | 0.027 | 149 | 150 | 99 |
| S 16 + 800 | 0.140 | 826 | 800 | 103 |
| S 03 + 0 | 0.024 | 141 | | |
| S 03 + 150 | 0.055 | 338 | 291 | 116 |
| S 03 + 800 | 0.102 | 929 | 941 | 99 |
| S 09 + 0 | 0.003 | 6 | | |
| S 09 + 150 | 0.031 | 185 | 156 | 118 |
| S 09 + 800 | 0.144 | 902 | 806 | 112 |
| S 04 + 0 | 0.000 | 0 | | |
| S 04 + 150 | 0.030 | 173 | 150 | 115 |
| S 04 + 800 | 0.149 | 865 | 800 | 108 |
| S 10 + 0 | 0.000 | 0 | | |
| S 10 + 150 | 0.028 | 164 | 150 | 110 |
| S 10 + 800 | 0.150 | 865 | 800 | 108 |

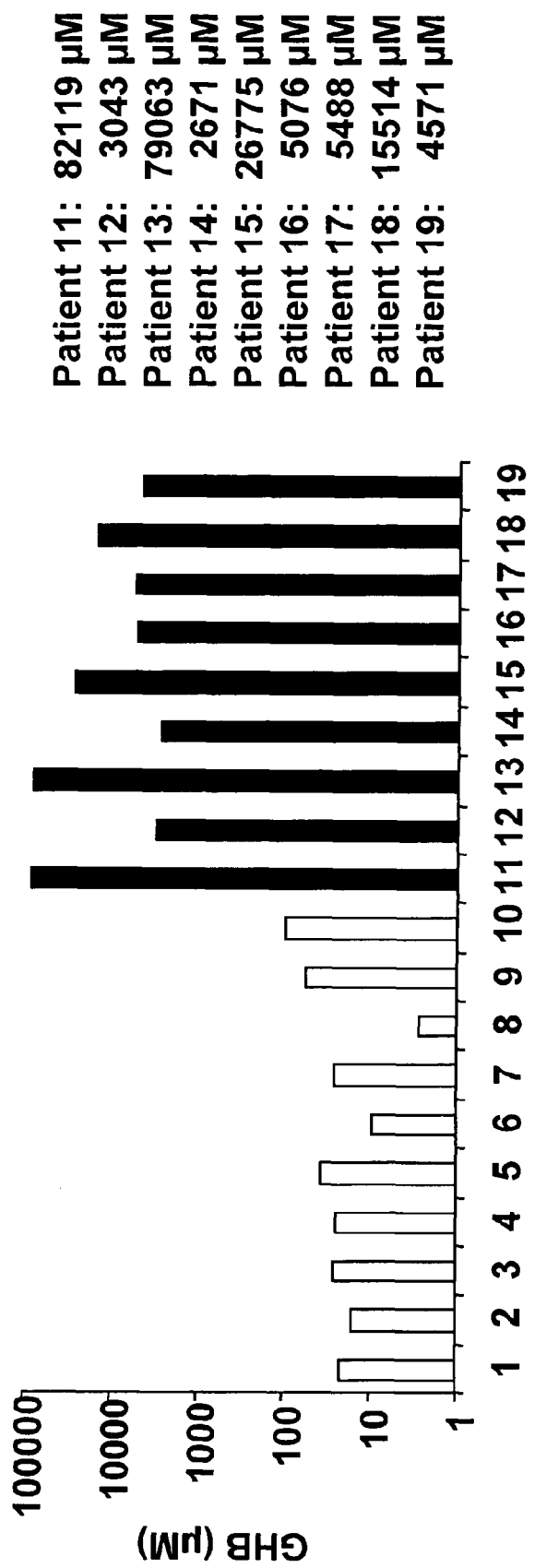

METHODS FOR DETERMINING THE CONCENTRATION OF GAMMA-HYDROXY BUTYRIC ACID (GHB) IN A SAMPLE

CROSS REFERENCE TO RELATED APPLICATIONS

This application is a U.S. National Phase Application of PCT/EP2010/055436, filed Apr. 23, 2010, which claims priority European Patent Application No. 09005884.3, filed Apr. 28, 2009, the contents of such applications being incorporated by reference herein in their entirety.

FIELD OF THE INVENTION

The invention relates to methods to determine the concentration of gamma-hydroxy butyric acid (GHB) in a sample as well as compositions and a kit suitable for carrying out said methods. The invention relates moreover to the use of the methods for application to a microtiter plate or an autoanalyzer (equipment for random access analysis, often used in clinical laboratories).

BACKGROUND OF THE INVENTION

Gamma-hydroxy butyric acid (4-hydroxybutanoic acid, $C_4H_8O_3$), commonly abbreviated GHB, is an endogenous substance and a therapeutic drug which is illegal in multiple countries and a naturally occurring substance found in the central nervous system, vine, beef, small citrus fruits and almost all other living creatures in small amounts. It is currently regulated in the US and sold by Jazz Pharmaceuticals under the name Xyrem.

In a medical setting, GHB is used as a general anesthetic, to treat conditions such as insomnia, clinical depression, narcolepsy, and alcoholism, and to improve athletic performance.

In Italy, GHB is used in the treatment of alcoholism (50 to 100 mg per kg per day in three or more divided doses) under the trade name Alcover (ATCN 07 BB), both for acute alcohol withdrawal and medium to long term detoxification. In the United States, the Food and Drug Administration (FDA) permits the use of GHB under the trade name Xyrem to reduce the number of cataplexy attacks in patients with narcolepsy.

When GHB is used in its sodium or potassium salt form, a significant quantity of excess sodium or potassium may be consumed, which should be taken into consideration by people with heart insufficiency, hypertension or reduced renal function. The bioavailability of sodium GHB is considerably reduced when it is consumed with food, and so it is advised to wait at least two hours after eating before consuming the dose. Because of its strong sedative effects, patient should not drive or operate heavy machinery for at least six hours after taking sodium GHB.

Adverse effects from Xyrem in clinical trials included: headache, nausea, nasopharyngitis, dizziness, somnolence, vomiting, urinary incontinence, confusion, dyspnea, hypoesthesia, paresthesia, tremor, vertigo, and blurred vision.

Gamma-hydroxy butyrate (GHB) is also an illicit chemical that has become a major cause of drug related comas in the US and other countries. In fact, the number of GHB overdoses in the United States has now out-paced overdoses from MDMA (Ecstasy). GHB was rejected by the American medical community in the 1960s, but has become popular among many people for its ability to cross the blood brain barrier freely and depress consciousness, resulting in euphoria, but also toxic effects. It is also touted on the Internet as a sleep aid and anti-depressant and weight loss product although these uses are not substantiated by proven scientific studies and may carry potentially deadly twists. Starting first as an alternative to steroids in the late 1980s when steroids were being controlled, GHB has grown into a multiheaded medical nightmare draining emergency room services, shattering the lives of those who have lost loved ones to it and terrifying families/friends of those addicted to it. Yet, it is still a mystery to most law enforcement officers, medical/coroner personnel and parents.

Non-medically, GHB also acting as a central nervous system (CNS) depressant, is used as a drug of abuse. It has many street names including Liquid Ecstasy and Liquid X. At low doses, GHB can cause a state of euphoria, increased enjoyment of movement and music, increased libido and increased sociability. At higher doses, GHB my induce nausea, dizziness, drowsiness, agitation, visual disturbances, depressed breathing, amnesia, unconsciousness, and death. The effects of GHB can last from 1.5 to 3 hours or even longer, if large doses were consumed or if it was mixed with alcohol.

In general, the doses used recreationally are between 500 mg and 3000 mg, corresponding to approximately 0.5 to 3 ml of liquid if the concentration is 1 g/ml (which is not always the case). When used as a recreational drug, GHB may be found as a pure liquid or as GHB salt dissolved in water generally at a standardised concentration of 1 g/ml and so it is twice the strength of the drug, Xyrem, sold legally for medical use.

GHB salt dissolved in water and/or alcoholic beverages is notoriously dangerous as the concentration of GHB may not be known and so the actual dose of GHB being consumed can be difficult to judge accurately. Since GHB sold for recreational use is subject to no standardisation it can be impossible to verify the actual concentration of GHB solution bought on the illicit market. More than 1 g of sodium GHB can be dissolved in 1 ml of water and so sodium GHB solution can actually be stronger than pure GHB liquid. Other salt forms such as potassium GHB, calcium GHB and magnesium GHB have also been reported but the sodium salt is by far the most common.

Some chemicals are converted to GHB in the stomach and when circulating in the bloodstream. GBL or gamma-butyrolactone is one of such prodrugs. Other prodrugs include 1,4-butanediol (1,4-B). There may be additional toxicity concerning these precursors. 1,4-B and GBL are normally found as pure liquids, although they may be mixed with other more harmful solvents when intended for industrial use, e.g. as paint stripper or varnish thinner.

GHB can be produced in clandestine labs and it is claimed that most of the GHB used in the US is illegally manufactured within its borders. While available as a prescription for sleep disorders in some other countries, GHB was banned (in the US) by the FDA in 1990 because of the dangers associated with its use. However, on Jul. 17, 2002, GHB was approved for treatment of cataplexy often associated with narcolepsy.

GHB was first synthesised in France more than 40 years ago as a possible anesthetic but because of its undesirable side effects was rejected by the American medical community. Its legal use anywhere is dwindling as countries are beginning to recognize the problems. GHB resurfaced in 1987 as an orphan drug being researched to treat the combination of sleep disorders known as narcolepsy/cataplexy. At about the same time, steroid users were told that it might enhance the body's production of growth hormones (in-deep-sleep-state). However, due to growing numbers of overdoses, it was ordered off the shelves of stores in November 1990. Unfortunately, it has gained status as a recreational drug and as a rape drug and has become dangerously common. As a result of increased restrictions on GHB itself, its 'analogs' or chemical relevants that can be converted to GHB in the body, have become increasingly prevalent.

The action of GHB has yet to be fully elucidated. GHB clearly has at least two sides of action, stimulating the latey characterized and aptly named "GHB receptor" as well as the $GABA_B$ receptor. GHB, if it is indeed a neurotransmitter, will normally only reach concentrations high enough to act at the GHB receptor as it has relatively weak affinity for $GABA_B$ receptor. However, during recreational usage, GHB can reach very high concentrations in the brain, relative to basal levels and can act at the $GABA_B$ receptor as well. The action of GHB at the $GABA_B$ receptor are probably responsible for its sedative effects. GHB-mediated $GABA_B$ receptor stimulation inhibits dopamine release as well as causes the release of natural sedative neurosteroids (like other $GABA_B$ agonists such as Baclofen). In animals, the sedative effects of GHB can be stopped by $GABA_B$ antagonists (blockers).

The relevance of the GHB receptor in the behavioural effects induced by GHB is more controversial. It seems hard to believe, that the GHB receptor is not important when it is densely expressed in many areas of the brain, including the cortex, as well as it being the high affinity site of GHB action. There has only been limited research into the GHB receptor. However, there are evidences that it causes the release of glutamate which is a stimulatory neurotransmitter. Drugs which selectively activate the GHB receptor but not the $GABA_B$ receptor such as trans-4-hydroxycrotonic acid and 4-(p-chlorobenzyl)-GHB cause convulsions in animals and do not produce GHB-appropriate responding.

Activation of the GHB receptor does not alone explain GHB's addictive properties; research using selective $GABA_B$ agonists and analogues of GHB, which are selective agonists for the GHB receptor but do not activate $GABA_B$, suggested both the GHB receptor and the $GABA_B$ receptor are important for dopamine release and consequently abuse liability. Compounds which activate only one of the receptors but not both, do not seem to induce acute dopamine release or to exert the abuse potential typical for GHB itself.

Generally high doses of GHB are sedative through its action at the $GABA_B$ receptor, while lower doses are stimulatory through activation of GHB receptors. This may explain the paradoxical mix of sedative and stimulatory properties typical for GHB intoxication, as well as the so called "rebound" effect, experienced by individuals using GBH as a sleeping agent, when they awake suddenly after several hours of GHB-induced deep sleep. This is due to the fact, that the concentration of GHB in the system decreases because of metabolism below a threshold for stimulating $GABA_B$ receptor function, and then stimulates the GHB receptor leading to wakefulness.

The depressant effects of GHB on the brain in low doses produce a high or euphoric feeling as inhibitions are depressed. When the dose is increased, profound coma results. The heart rate may also be depressed or slowed down. Effects on the nervous system may result in a spasm of muscle contractions called myoclonus, producing seizure-like movements. Other effects such as confusion, amnesia, vomiting and irregular breathing are dangerous when combined with the major depressant effects of GHB. Other drugs in combination with GHB, particularly alcohol, may worsen the depressive effect and increase the possibility of a fatal outcome. The desired effects for GHB in low doses may sound inviting, but the consequence of a (falsely) high dose may be death. The dosage response of GHB is quite steep, meaning that a tiny increase in dose may cause a dramatic increase in symptoms and risk. Variable effects mean that a teaspoon might be perfect one time, but may become an overdose the next time. It is also important to be aware of the consequences that occur when GHB is mixed with other chemicals. For instance, mixing GHB with alcohol or other depressants is even more likely to result in death. The effects last about four hours and can resolve quite suddenly.

The drug has furthermore recently been referred in the media to as a date rape drug, in much the same way as alcohol and the drug, Rohypnol. GHB by itself has a soapy or salty taste, but diluted in solutions it is almost tasteless and, therefore, when mixed in some drinks it is difficult to detect. Moreover, identification of GHB after consumption is complicated by the short duration of time that it persists in body fluids. So far, several testing methods have been developed within the art: methods for screening of gammy-hydroxybutyric acid (GHB) in body fluids or hair but also in beverages.

Kintz et al. described for example a testing method for GHB in hair by gas chromatography (GC)/mass spectroscopy (MS). The method requires decontamination of the hair sample with dichloromethane followed by overnight incubation in 0.01 N NaOH in the presence of GHB-d6, followed by neutralisation and extraction in ethyl acetate under acidic conditions (J. Forensic Sci., 2003, January; 48(1): 195-200), which is incorporated by reference. A similar method has been developed by Shen et al. (Fa Yi Xue Za Zhi; 2006 February; 22(1): 48-51), which is incorporated by reference who provide a GC/MS assay for GHB in hair. Both methods do not only have the disadvantage that GC/MS testing methods are time consuming and elaborate, but also that the hair sample can soonest be collected one month after the alleged event in order to sample the corresponding period of the regular growing. Therefore, real-time and onsite testing is not possible.

Until now, ways to measure GHB in blood and urine have been almost limited to chromatographic methods, such as GC-MS, LC/LC-MS, HPLC, HPLC-MS or capillary electrophoresis (CE).

Testing methods for determination of GHB in blood and urine samples were for example developed by Kankaanpaa et al. (Forensic Sci Int. 2007 Aug. 6; 170 (2-3): 133-8), which is incorporated by reference. This method also uses a GC/MS analysis after several extractions, acidification and centrifugation steps. Similar methods (GC/MS in association with several conditioning and/or preparation steps) are provided by Liu et al. (Fa Yi Xue Za Zhi; 2007 April; 23(2): 120-2, 129), which is incorporated by reference, Paul et al. (J Anal Toxicol. 2007 July-August; 30(6): 375-9), which is incorporated by reference, Ferrara et al. (J Farm Biomed Anal. 1993 June; 11(6): 483-7), which is incorporated by reference, Villain et al. (J Chromatogr B Analyt Technol Biomed Life Sci. 2003 Jul. 15; 792(1): 83-7), which is incorporated by reference, McCusker et al. (J Anal Toxicol. 1999 September; 23(5): 301-5), which is incorporated by reference, Elian (Forensic Sci Int. 2000 Apr. 10; 109(3): 183-7), which is incorporated by reference and Blanchet et al. (J Chromatogr B Analyt Technol Biomed Life Sci. 2002 Apr. 5; 769(2): 221-6), which is incorporated by reference. Gas-chromatographic (GC) methods were also commonly used for the detection of GHB in beverages and/or drinks (e.g. Liu et al., Fa Yi Xue Za Zhi, 2007 April; 23(2): 120-2, 129), which is incorporated by reference.

Further testing methods for GHB content include a colour test for rapid screening of GHB in drinks and urine characterized in that GHB was converted into an acidic solution to GBL which reacted with hydroxylamine hydrochloride in presence of sodiumhydroxide forming hydroxamate. A purple complex was formed when hydroxamate reacted with ferric chloride in acidic condition (Zhang et al.; Fa Yi Xue Za Zhi, 2006 December; 22(6): 424-7), which is incorporated by reference.

Further, a method of determination of GHB in human urine by capillary electrophoresis (CE) with indirect UV detection and confirmation with electrospray ionisation ion-trap mass spectrometry is known within the art (Baldacci et al., J Chromatogr A, 2003 Mar. 21; 990(1)-2: 99-110), which is incorporated by reference. The assay is based on liquid extraction and capillary zone electrophoresis (CZE) with indirect UV absorption detection. The background electrolyte is composed of 4 mM nicotinic acid (compound for indirect detection), 3 mM spermine (reversal of electro-osmosis) and histidine (added to reach a pH of 6.2). Having a 50 micron I.D. capillary of 40 cm effective length, 1-octanesulfonic acid as internal standard, solute detection at 214 nm and a diluted urine with a conductivity of 2.4 mS/cm, GHB concentrations ≥2 µg/ml can be detected.

In addition, an enzyme based assay for GHB detection has been developed by Bravo et al., wherein the GHB content of a sample is determined in a two step testing method using GHB dehydrogenase from *Ralstonia eutropha*. This method consists of at least two consecutive steps, wherein the first step consists in contacting the sample with the GHB-oxidoreductase and an oxidized cofactor resulting in the reduction of the oxidized cofactor and wherein the second step consists in contacting the sample and the reduced cofactor with a second oxidoreductase and a chromogen or dye resulting in the formation of a detectable compound (Bravo et al., J Forensic Sci, March 2004, Vol. 49, No. 2: 379-87), which is incorporated by reference. This method is further patented by U.S. Pat. No. 6,703,216 B2, which is incorporated by reference.

All of the methods already known within the state of the art require either extensive equipment, and/or highly skilled personnel and/or take a long time to conduct. The need for a new, simple and rapid method which can also be accomplished by less qualified laboratory personnel, does not require extensive equipment to conduct and—in addition very fast—making the method also suitable for emergency testing.

SUMMARY OF THE INVENTION

It is therefore an object of the present invention to provide a method for the determination of GHB, which is easily conductible and does not require extensive and costly equipment for either the application to a microtiter plate reader or an autoanalyzer. It is further an object of the present invention to provide a kit and composition suitable for the conduction of the method of the present invention.

The method should have the further advantages to be easily adaptable to clinical chemistry analyzers and showing good correlation with standard chromatographic methods. Moreover, GHB determination should be possible for either high or low levels in samples.

Surprisingly it has been found that it is possible to detect the GHB content of a sample by incubating the sample with an enzyme capable of converting GHB to succinic semialdehyde (SSA) and an oxidized cofactor resulting in the reduction of the oxidized cofactor and measuring the quantity of the reduced cofactor. The quantity of the reduced cofactor measure can then be directly correlated with the concentration of GHB in the sample.

DETAILED DESCRIPTION OF THE INVENTION

The present invention therefore provides a method to determine the concentration of gamma-hydroxy butyric acid (GHB) in a sample, whereas the method comprises the steps of:

a) incubation of the sample and an enzyme capable of converting GHB to succinic semialdehyde (SSA) and reducing an oxidized cofactor,
b) measuring the quantity of the reduced cofactor and
c) correlating the measured quantity of the reduced cofactor with the concentration of GHB in the sample.

The present invention further provides a composition for assaying a sample for GHB, comprising the following components:
a) an enzyme capable of converting GHB to succinic semialdehyde (SSA), and
b) an oxidized cofactor.

Moreover, the present invention provides a kit, suitable for carrying out the method of the present invention.

The invention also relates to the use of the method of the present invention for application to a microtiter plate or an autoanalyzer (random access analysis, often used in clinical laboratories for measuring clinical chemical parameters such as electrolytes, enzymes, drugs of abuse, therapeutic drugs, tumor markers, hormones, cardiac markers etc.).

In the method of the present invention the sample can be either taken from any kind of body fluids and also from any kind of beverages including alcohol-containing beverages or any kind of food extracts. In case the sample is taken from body fluids, the sample is preferably selected from the group consisting of blood, serum, plasma, lymph, cells or tissue derived extracts, bone marrow fluid, saliva, eyeball fluid, semen, brain extract, spinal fluid, joint fluid, thymus solution, abdominal dropsy or purified materials and liquor amnii, but is not limited thereto, wherein blood, serum or plasma and spot urine are most preferred. Possible plasma samples include EDTA, citrate and Heparin plasma. When the sample is taken from beverages or beverages-like products the sample is preferred selected from the group consisting of drinks, either alcohol-containing drinks such as beer, wine, liquor as well as alcohol-containing mixed drinks such as cocktails and "alcopops" or from non-alcoholic beverages such as carbonated or fizzy drinks like lemonade, carbonated mineral water, Coca Cola®, Ginger Ale®, Bitter Lemon®, Tonic Water® or Sprite®, fruit juice, but is not limited thereto. In the sense of the present invention, it is also possible to take the sample from beverages-like food products such as buttermilk, milk, drink-yoghurt, yoghurt and cream. Further possible samples are tea and tea-containing products, cocoa and cocoa-containing products as well as coffee, coffee substitutes and other coffee-containing products.

In the sense of the present invention GHB can originate from GHB or an analogue thereof. Further the term "GHB" comprises the terms "gamma-hydroxy butyric acid", "gamma-hydroxy butyrate", "4-hydroxy butyric acid", "oxybutyrate", "gamma-hydroxy sodium butyrate", gamma-hydroxy butyrate sodium", "gamma-hydroxy butyric acid decomposition product", "gamma-hydroxy butyric acid monosodium salt", "4-hydroxy butanoic acid", "4-hydroxybutanoate", "4-hydroxybutyrate sodium", "4-hydroxy butyric acid monosodium salt", "4-hydroxy butyric acid sodium salt", "sodium gamma oxybutyrate" and the like, but is not limited thereto, which can be used interchangeably. Further comprised are substances denoted by the following terms and commercial names: "4HB", "4-03-00-00774 (Beilstein Handbook Reference)", "4-OHB", "502-85-2", "52352-27-9", "591-81-1, "AIDS-156012", "AIDS 156012", "BRN 1720582", "C00989", "CHEBI:30830", "DEA No. 2100", "EB 27", "Gam-OH", "gamma-OH", "LMFA01050006", "NSC84223", "Somsanite", "WY 3478", "WY-3478", "sodium oxybate" and the like, but are not limited thereto. Further comprised, and detectable by the methods of the present invention, are GHB analogues, salts and isomers thereof, which are structurally related to GHB, produce an identic or highly similar pharmacological effect and which can be used as a substrate for the enzyme as described in present claim 1 of the present invention. The GBH salts can be GHB, as described before or an analogue thereof as well as proforms or precursors which can be converted to GBH (e.g. ethers or amides) and precursors to GHB including, but without limitation, "gamma butyrolactone", "1,4-butaneol" and any other compounds which are structurally related to GHB, produce an identical or similar pharmacological effect (either directly or after metabolism) and which can be detected by the methods provided the present invention either directly or after preparing steps. The terms "GBL", "gamma butyrolactone", "4-hydroxy butyric acid lactone", "1,4-butanolide", "4-butyrolactone" and the like are used interchangeably and refer to "dihydro-2(3H)-furanone". The term "precursor" relates to compounds which allow to produce GHB chemically or after metabolism in the body.

In the sense of the present invention, levels between 5 μM (~0.5 mg/L) and 100000 μM (~10 g/L), preferably between 25 μM and 50000 μM and more preferred between 50 μM and 20000 μM can be determined. When testing urine samples, the concentration of GHB which can be determined is preferably between 0 μM and 2000 μM, more preferred between 20 and 500 μM, further preferred between 30 and 150 μM and most preferred 100 μM when testing therapeutic levels and a cut-off of 100 μM is preferably used to discriminate between endogenous and/or therapeutic levels and positive levels with potential toxic effects. When testing plasma or serum samples, the concentration of GHB which can be determined is preferably between 0 μM and 1000 μM, more preferred between 10 and 500 μM, further preferred between 20 and 100 μM and a cut-off of 50 μM is preferably used to discriminate between endogenous and/or therapeutic levels and positive levels with potential toxic effects. Samples with a too high concentration for direct analysis can be diluted by means known to a person skilled in the art.

The enzyme used in the methods of the present invention can be any enzyme capable of converting GHB to succinic semialdehyde (SSA) and reducing an oxidized cofactor. Examples for such enzymes are oxidoreductases. The term "oxidoreductase" in the sense of the present invention comprises any enzyme able to catalyze the transfer of electrons from one molecule (reductant, also called hydrogen acceptor or electron donor) to another (oxidant, also called hydrogen donor or electron acceptor). Particularly preferred oxidoreductases include dehydrogenases and reductases wherein GHB dehydrogenase (GHB-DH), SSA-reductase, glucuronate reductase and aldehyde reductase are most preferred. A mixture of one or more enzymes, as defined before, can also be used in the method of the present invention.

The enzyme suitable for the method of the present invention can be either derived naturally or recombinant but is preferred derived from a synthetically manufactured gene construct (plasmid). In the sense of the present invention any method known in the art for the preparation of recombinant enzymes can be used. These methods include, but are not limited to, the synthesis of compounds based on starting material found in nature and the preparation of fully synthetic systems.

In the sense of the present invention, two different methods for the production of the enzymes are preferred. In the following, the methods preferred in the sense of the present invention are exemplarily outlined for the production of the enzyme GHB-DH, starting with isolating, cloning and sequencing of GHB-DH (producing a gene construct):

Isolating, cloning and sequencing the GHB-DH is carried out from *Ralstonia eutropha, Pseudomonas putida* and/or *Bordetella parapertussis*. Upstream and downstream primers for GHB-DH can be used to amplify the gene. GHB-DH is then produced as recombinant His-tagged fusion protein and purified using His-binding magnetic beads or superflow column. The coding sequence of the genes can be cloned into pQE-30 UA vector and recombinant GHB-DH is expressed and purified as indicated.

1. Expression in *E. coli*

The construct from *Ralstonia eutropha, Pseudomonas putida* and/or *Bordetella parapertussis* is used as a starting material. According to this method, there are three possible variables for optimization of GHB-DH expression: (1) *E. coli* strains (M15, BL-21 and XL1-blue MRF'), (2) inductor concentration (IPTG) and (3) incubation temperature for induction (18° C.-37° C.). The construct pQE-30UA vector including the sequence from *Ralstonia eutropha, Pseudomonas putida* and/or *Bordetella parapertussis* is transformed e.g. in XL1-blue with and without the lac repressor helper plasmid pREP4. Expression of the correct recombinant protein is verified by SDS-PAGE and western blot using anti-His-Tag antibodies. In parallel, small scale IMAC is carried out of solubilized GHB-DH aggregates from the XL1-blue expressions. Then, the plasmid will be retransformated in the selected set of expression strains.

2. Expression in *Pichia pastoris*

The vector pPICZalpha A, which contains the alpha-factor secretion signal to target recombinant proteins is given to the growth medium. Multiple copies of the gene of interest can be integrated in a single cell. High number of copies can be selected by increasing Zeocine concentration. The GHB-DH sequence from the original construct (see above) is recloned into the vector pPICZalpha A without his His-Tag labelling. The transformation in *P. pastoris* is performed by chemical methods and selected by resistance to Zeocine.

A cofactor in the sense of the present invention is to be understood as a non-protein chemical compound that is bound tightly to an enzyme and is required for its catalytic activity. They can be considered as "helper" molecules and ions, respectively, that assist in biochemical transformations. An oxidized cofactor in the sense of the present invention is any cofactor capable of being reduced within in the method of the present invention.

Cofactors, which can be used in the method of the present invention include nicotinamide cofactors, flavin cofactors, quinone cofactors and oxoacids, but are not limited thereto, whereas nicotinamide cofactors include nicotinamide adenine dinucleotide (NAD), nicotinamide adenine dinucleotide phosphate (NADP), nicotinamide 1, N6-ethenoadenine dinucleotide and nicotinamide 1, N6-ethenoadenine dinucleotide phosphate, but are not limited thereto. Flavin cofactors include those cofactors comprising a flavin group or an active portion thereof. Examples for flavin cofactors in the sense of the present invention are riboflavin, isoalloxazine, flavin mononucleotide (FMN) and flavin adenine dinucleotide (FAD), but are not limited thereto. In the sense of the present invention, quinone cofactors are to be understood as cofactors including a quinone group. Examples of quinone cofactors are pyrroloquinoline quinine (PQQ), but are not limited thereto. Examples of oxoacids include alpha-ketoglutarate, but are not limited thereto. Analogues of cofactors, which can be used in the method of the present invention, are also within the scope of the present invention.

Particularly preferred cofactors are nicotinamide adenine dinucleotide ($NAD^+$) and nicotinamide adenine dinucleotide phosphate (NADP).

In the sense of the present invention $NAD^+$ consists of two ribose rings, one with adenine attached to its 1' carbon atom and the other is nicotinamide at this position. These two sugar heterocycle moieties are joined together by a bridge of two phosphate groups through the 5' carbons, In $NAD(P)^+$ the ribose ring attached to the adenine has an additional phosphate group at the 2' position. Analogs of the cofactors are nicotinamid adenine dinucleotide ($NAD^+$) and nicotinamide adenine dinucleotide phosphate (NADP) are, for example, 3-acetylpyridine-NADH, 3-acetylpyridine NADPH, 3-pyridinealdehyde-NADH, 3-pyridinealdehyde-NAPDH, thionicotinamide-NADH and thinicotinamide-NADPH, but are not limited thereto and can also be use within the method of the present invention. Further, a mixture of one or more cofactors and analogues thereof, respectively, as defined before, can be used in the method of the present invention.

In method of the present invention NAD+ is used in a concentration of from 0.001 mM to 1000 mM, preferably of from 0.01 mM to 100 mM, more preferred of from 0.1 mM to 10 mM and most preferred at a concentration of 2 mM.

In the method of the present invention the cofactor $NAD(P)^+$ is used to accept electrons and therefore $NAD(P)^+$ is reduced to NAD(P)H. The method of the present invention can generally be carried out in several different ways for example in a microtiter plate or an auto-analyzer. In this context the microtiter (or microplate) is a flat plate with small tubal "wells" used as small test tubes. Each well of a microplate typically holds somewhere between a few and a few hundred microliters of liquid. Microplates can be handled by robots but also by hand. The robots may be liquid-handlers which aspirate or dispense liquid samples from and to these plates, or "plate movers" which transport them between instruments. The event taking place in the wells of the plate can afterwards be detected by special microtiter plate readers. Preferably a high-intensity lamp sends light through the microtiter well and the light absorbed or emitted by the reaction products built in the microplate well is quantified by a detector. Examples of suitable detection modes in the sense of the present invention are absorbance, fluorescence intensity, luminescence, time resolved fluorescence and fluorescence polarization wherein absorbance is particularly preferred.

An auto-analyzer in the sense of the present invention is an automated analyzer using special fluid handling and flow techniques. Examples of possible automated analyzers in the sense of the present invention are segmented flow analyzers, flow-injection-analyzers or automated analyzers with dialyzer modules. Typical auto-analyzers in the sense of the present invention can be Aeroset, Alcyon 300, C8000/16000 and Ci 8200/16200 from the company Abbott, Synchron Cx5, Synchron Cx4, Synchron Cx7, Synchron Lx20 and UniCell DxC800 from Beckman, Kone T20, T20 XT, T30 and T60 from Thermo, Reply Analyzer, AU 400, AU 600, AU 800, AU 640 and AU 2700/5400 from Olympus, Vitros Fusion 5.1 and Vitros 340 from Ortho, Cobas Mira, Hitachi 704, Hitachi 717, Hitachi 911, Hitachi 902, Hitachi 912, Hitachi 917, Cobas Integra 400/700/800, Modular P 800, Cobas C501, Cobas C111, Modular D2400, Cobas BIO, Cobas FARA and Cobas 6000 from Roche, Advia 1200, Advia 1650, Advia 1800 and Advia 2400 from Siemens (Bayer), Dimension RxL Dimension Xpand plus Dimension Vista 3000T and Dimension Vista 1500 from Siemens (Dade), Pentra 60 and Pentra 120 from ABX, Selectra E/XL from ELITech, Rx Daytona and RX Imola from Randox, and RA 500, RA 1000 and RA XT from Technicon, but not limited thereto. Auto-analyzers in the sense of the present invention are also named "clinical chemistry analyzers".

For the determination of the concentration of GHB in a sample, the quantity of the reduced cofactor has to be measured. Possible detection modes for measuring the quantity of the reduced cofactor are absorbance, fluorescence intensity, luminescence, time resolved fluorescence and fluorescence polarization, wherein absorbance is particularly preferred. The absorbance of the sample is preferably measured by the use of a spectrophotometer. In the sense of the present invention a spectrophotometer is a photometer (a device for measuring light intensity) that can measure intensity as a function of the color or more specifically the wavelength of light. There are many kinds of possible spectrophotometers in the sense of the present invention. Among the most important distinctions used to classify them are the wavelengths they work with, the measurement techniques they use, how they acquire spectrum and the sources of intensity variation they are designed to measure. Other important features of spectrophotometers include the spectral band-widths and linear range. Generally two different types of spectrophotometers can be used in the method of the present invention: single-beam and double-beam spectrophotometers. A double beam spectrophotometer measured the ratio of the light intensity on two different light paths and the single beam spectrophotometer measures the absolute light intensity. Although ratio measurements are easier and generally more stable, single beam instruments have advantages, for instance they can have a larger dynamic range.

The optical density of the sample treated according to the method of the present invention can be measured at the wavelengths from 1 nm to 1000 nm, preferably at a wavelength of 100 to 650 nm, more preferred at a wavelength of 280 to 450 nm and most preferred at a wavelength of 340 nm.

When carrying out the method of the present invention, one or more parameters can be individually selected, comprising the pH, buffer, ionic strengths, presence and concentration of one or more salts, presence and concentration of variations and cofactors, optional reagents, temperature, duration (incubation times) and volume of the reaction, but are not limited thereto. The parameters may be chosen in any combination to produce the desired results.

The pH of the reaction mixture can be chosen from pH 2 to pH 13, preferred from pH 8 to pH 12, and is most preferred at pH 10. To ensure the pH is suitable for the method of the present invention a buffer is preferably included within the assay. Possible, usable buffers include acetate, bicine, phthalate, borate, trichloroacetate, sulfosalicylate, phosphate, tartarate, citrate, succinate, maleic acid, 2,2-bis(hydroxymethyl)-2,2',2''-nitrilotriethanol, 3,3-dimethylglutaric acid, 3-N-morpholinopropanesulfonic acid (MOPS), malonic acid, 1,3-bis tris(hydroxymethyl)methylaminopropane (Bis-TRIS), tris(hydroxymethyl)aminomethane (TRIS), tris(hydroxymethyl)aminomethane-maleic acid (TRIS-maleate), tris(hydroxymethyl)aminomethane-malonic acid (TRIS-malonate), 3-N-(trishydroxymethyl)methylamino-2-hydroxypropane hydroxypropane sulfonic acid (TAPSO), 2-(tris(hydroxymethyl)methylamino)ethanesulfonic acid (TES), 1,4-piperazinebis(ethanesulfonic acid) (PIPES), 4-morpholinoethanesulfonic acid (MES), N-2-hydroxyethylpiperazine-N'-2-ethanesulfonic acid (HEPES), sulfate, amino acids (e.g. glycine), 2-amino-2-methyl-1,3-propanediol (AMPD), imidazole, triethanolamine, N,N-bis(2-hydroxyethyl)-2-aminoethanesulfonic acid (BES), N-cyclohexyl-2-aminoethanesulfonic acid (CHES), TRIS-HCl and others known to a person skilled in the art. Most preferred is AMPD buffer.

According to the method of the present invention, the incubation of the sample is carried out at a temperature of from 0°

C. to 100° C., preferred from 18° C. to 70° C., more preferred from 28° C. to 50° C., further preferred from 35 to 40° C. and most preferred at a temperature of 37° C.

According to the method of the present invention, the incubation time of the sample is between 1 second and several days, preferred between 10 seconds and 24 hours, more preferred between 30 seconds and 5 hours, further preferred between 1 minute and 60 minutes, 3 minutes to 12 minutes is also preferred and an incubation of 5 minutes to 8 minutes is most preferred.

The concentration of the enzyme used in the method of the present invention can be chosen from a range of 0.1 to 10000 μg/mL, preferably from 1 to 1000 μg/mL units per liter, more preferred from 10 to 100, further preferred from 30 to 80 and most preferred around 60 μg/mL.

According to the method of the present invention, the reaction volume can be chosen from 1 μl to 100 ml, preferred from 50 μl to 10 ml, more preferred from 100 μl to 1 ml and is most preferred 250 μl.

Within the scope of the present invention, additional reactants can be included in the method. Such reactants can include reactants able to convert precursors of GHB to form detectable compounds by the method of the present invention. To convert esters to GHB, esterases may be included to convert esters of GHB, internal esters such as GBL and the like to GHB. An amidase may be included to similarly convert amidated forms of GHB to GHB.

The substance to be optionally included within the method of the present invention may be chosen from the group comprising polymer agents such as polyvinylpyrrolidone, polyvinyl alcohol, gum Arabic, gelatin, algin, carrageenan, casein, albumin, methyl cellulose, uncapped polyethylene glycol, end-capped polyethylene glycol, polysaccharides (e.g. sucrose) and other natural and synthetic polymeric materials and combinations thereof and non-polymeric agents such as monosaccharides (e.g. glucose) and glycerol, but is not limited thereto. Further reagents may contain stabilizing agents and biocides.

Further, other optional components can be included within the method of the present invention such as proteins, e.g. bovine serum albumin, saccharides such as maltose, glucose, sucrose, trehalose, glycerol and the like, high molecular weight compounds such as polyethylene glycol and others known in the art and metal ions for example sodium, magnesium, potassium, calcium and others known in the art. In case metal ions are used as further optional components, these metal ions might act as enzyme activators and/or stabilizers. Further optional components are chelating compounds such as ethylene diamine tetra-acetic acid (EDTA). Preferably the saccharides are used in a concentration of from 0.1 to 50% (w/v), preferred from 0.15 to 20% (w/v), more preferred from 1 to 5% (w/v). Proteins are preferably used in a solution with a concentration from 0.001 to 50% (w/v), preferred from 0.0015 to 20% (w/v), more preferred from 0.01 to 2% (w/v). Metal ions are preferably used in a solution having a metal ion concentration of from 0.001 to 1000 mM, preferably from 0.1 to 100 mM and most preferred from 0.15 to 80 mM. EDTA is preferably used in a solution with a concentration of from 0.001 to 50 mM, preferably from 0.01 to 2 mM, further preferred from 0.1 to 1.5 mM and is most preferred 0.8 mM.

In addition, further steps to those mentioned above can be carried out. Further steps can be for example, but not limited thereto, chosen from the group consisting of:

a special treatment of the sample such as sample deproteinization or heating depending on the performance of the single test; to optimize the reproducibility of enzyme purification by stronger lysis of transformed bacteria culture, by eluting the expressed proteins by Ni2+-charged columns under native and denaturing conditions and/or by adding proteinase inhibitors and/or preservatives (e.g. NaN3) to the eluted proteins—integrity of expressed fusion protein and protein contaminants can be evaluated by SDS-PAGE analysis or by evaluating a method to solve the formation of inclusion bodies and refold them; to minimize GBH-DH independent enzymatic or non-enzymatic formation of NADH in the sample by pre-incubating the sample with NAD+ in the absence of GHB-DH, by diluting the sample, by adding an inhibitor of glycolytic enzymes including lactate dehydrogenase (e.g. oxalic acid) in combination with EDTA or by heat-inactivating the sample; adding a hemoglobin suppressor such as nitrites and sodium nitrite salts; addition of further suitable buffers such as TRIS-HCl, CAPS, CAPSO and/or AMP for alkaline pH. In the sense of the present invention all additional steps as mentioned above can be carried out—alone or in any combination—within the method of the invention.

The present invention also relates to a kit suitable for carrying out the method as described above. A kit suitable for carrying out the method of the present invention includes at least an enzyme capable of converting GHB to succinic semialdehyde (SSA) and an oxidized cofactor. The kit may also contain optional components such as buffer substances, additional reagents capable of converting GHB precursors to detectable forms, substances to improve the capability of the assay, proteins, saccharides, high molecular weight compounds, metal ions and chelating compounds which were all described above in greater detail, but are not limited thereto.

The present invention also relates to compositions suitable for assaying a sample of GHB comprising at least an enzyme capable of converting GHB to succinic semialdehyd (SSA) and an oxidized cofactor. The enzyme contained in the composition is preferably an oxidoreductase, more preferred a dehydrogenase and most preferred a GHB dehydrogenase (GHB-DH). Further compounds and reagents as described above in greater detail, can additionally be contained in the composition. The oxidized cofactor contained in the composition is preferable NAD+.

The present invention also relates to the use of the method as described above for application in a microtiter plate or on an auto-analyzer.

BRIEF DESCRIPTION OF THE DRAWINGS

The present invention is further described by the following figures, though not limited thereto. It is understood, that the figures do have exemplary character and are for illustrative purposes only.

FIG. 3 shows two assay formats adapted for auto-analyzers (clinical chemistry analyzers). Both formats describe a one-reagent assay performed on the Kone T30 analyzer. Before placing the reagent on the auto-analyzer the reagent mix containing the buffer, inhibitors, cofactor and enzyme has to be prepared by mixing Ra, Rb and Rc or Ra' and Rb' as indicated. Then, the reagent is contacted with the samples or calibrators, incubated for and measured after the indicated time periods in the auto-analyzer. Abbreviations: OxA (oxalic acid); Cal (calibrators).

FIG. 4 shows a two-reagent assay format performed on the Kone T30 auto-analyzer. Before placing the reagent mix R1 on the auto-analyzer the reagent R1a containing the buffer and inhibitors and the reagent R1b containing the cofactor has to be prepared by mixing R1a and Rb as indicated. Then, the reagent R1a:R1b is contacted with the samples or calibrators for 2 minutes before adding the reagent R2 containing GHB-DH. The final reaction mix is incubated and measured for another 6 minutes in the auto-analyzer. Abbreviations: OxA (oxalic acid); Cal (calibrators); Con L (urine control containing ~150 µM GHB; Con H (urine control containing ~800 µM GHB).

FIG. 6 shows the results of a series of assays (spiking recovery experiments) run on a clinical chemistry analyzer (Kone T30, Thermo; two-reagent assay format; total incubation time was 8 minutes) to validate the accuracy of the method for urinary samples. In this example, urines from normal donors (n=5) were spiked with 0, 100, 500 and 1000 µM of GHB. Percent (%) spiking recovery was calculated as %-value (O/E) of observed (O) GHB concentration to expected (E) GHB concentration in spiked samples.

FIG. 7 shows the results of a series of assays (spiking recovery experiments) run on a clinical chemistry analyzer (Kone T30, Thermo; two-reagent assay format; total incubation time was 8 minutes) to validate the accuracy of the method for serum samples. In this example, serum from normal donors (n=6) were spiked with 0, 150 and 800 µM of GHB. Percent (%) spiking recovery was calculated as %-value (O/E) of observed (O) GHB concentration to expected (E) GHB concentration in spiked samples.

FIG. 11 shows the comparison of endogenous levels of GHB in urine samples from normal donors (n=10) with GHB concentrations in urine samples from intoxicated patients (n=9). All samples were measured with the enzymatic method of the present invention (Kone T30, Thermo; two-reagent assay format; total incubation time was 8 minutes). GHB concentrations measured are given in µM. Patient samples with an initial concentration above 2000 µM were 5 to 100 times diluted with 0.9% NaCl solution and re-analyzed.

Figure 1:
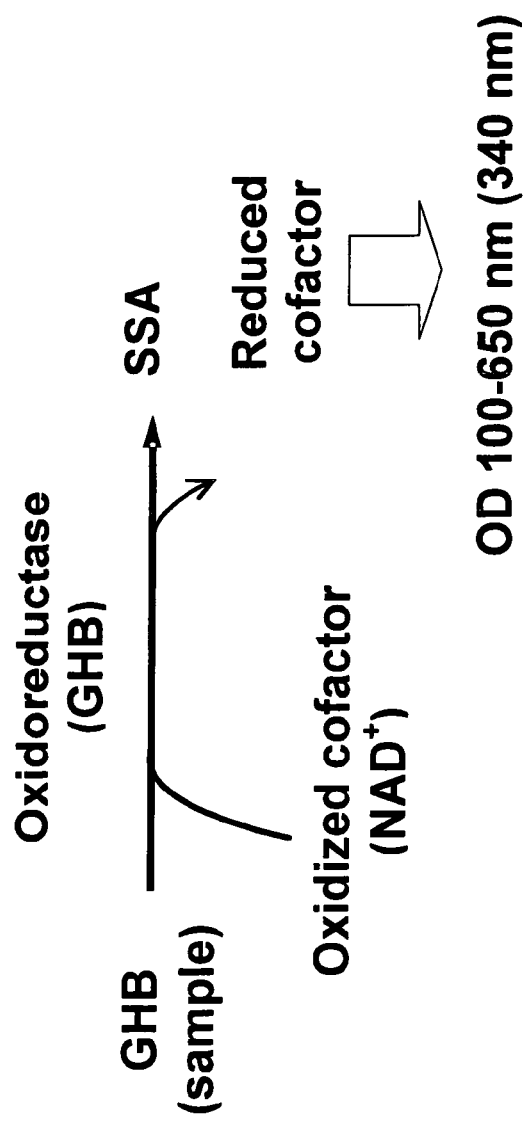
FIG. 1 shows the principle of the determination of the GHB concentration in a sample (e.g. serum, urine, beverage). In the assay, the oxidoreductase (GHB dehydrogenase, GHB-DH; EC 1.1.1.61) oxidizes GHB to succinic semialdehyde (SSA) using NAD+ as cofactor. There is a direct relationship between the drug (GHB) concentration and the enzyme activity. The reaction is started by adding the enzyme and GHB-DH activity is determined spectrophotometrically at 340 nm by measuring its ability to convert NAD+ to NADH.
Figure 2:
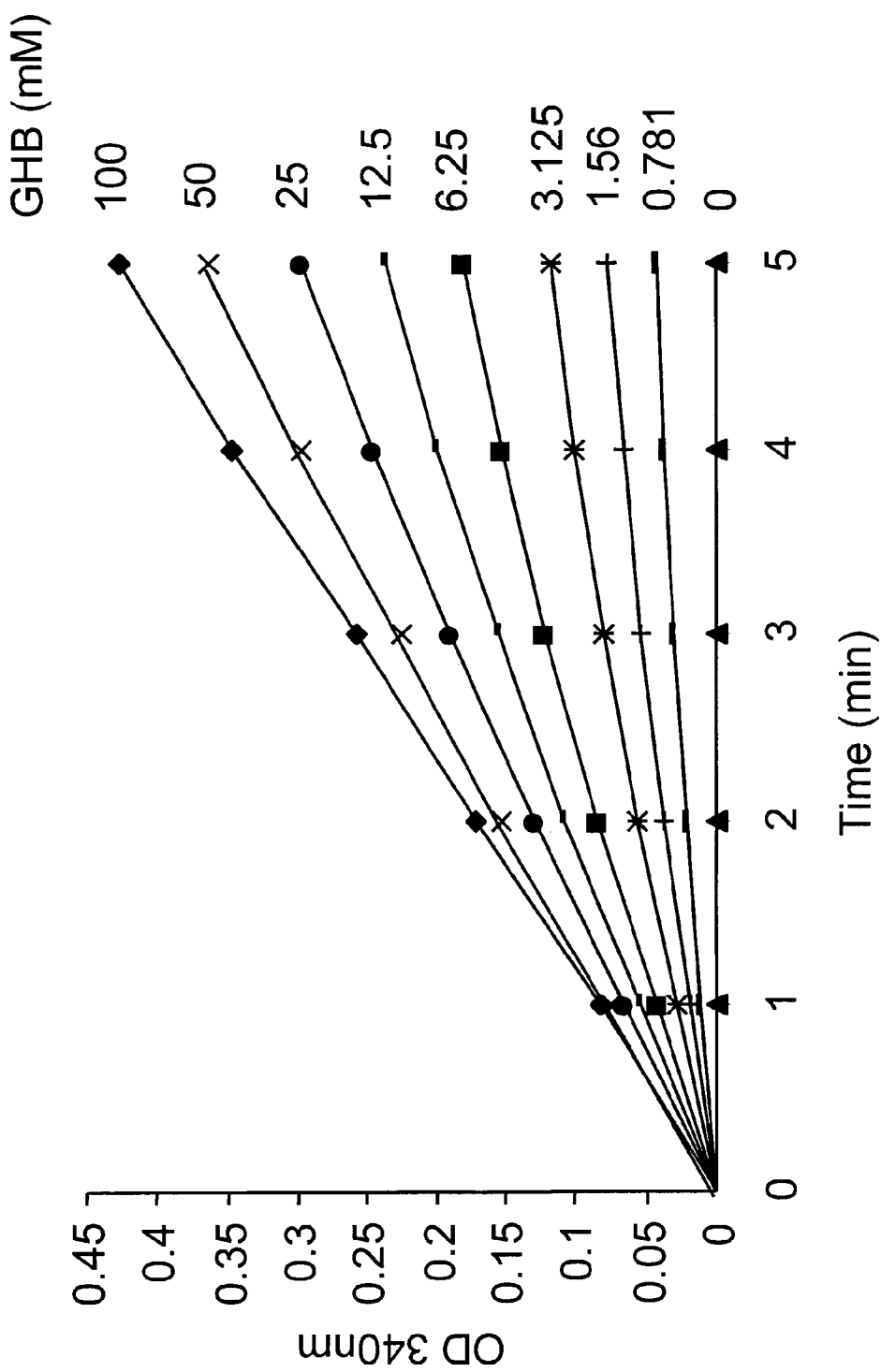
FIG. 2 shows a microplate assay regarding the kinetics of GHB-DH. The GHB-DH activity in function of GHB concentrations added to the reaction volume was measured for 5 minutes in a microplate assay. GHB concentrations (expressed in mM) which are used in the assay are indicated on the right site.
Figure 5:
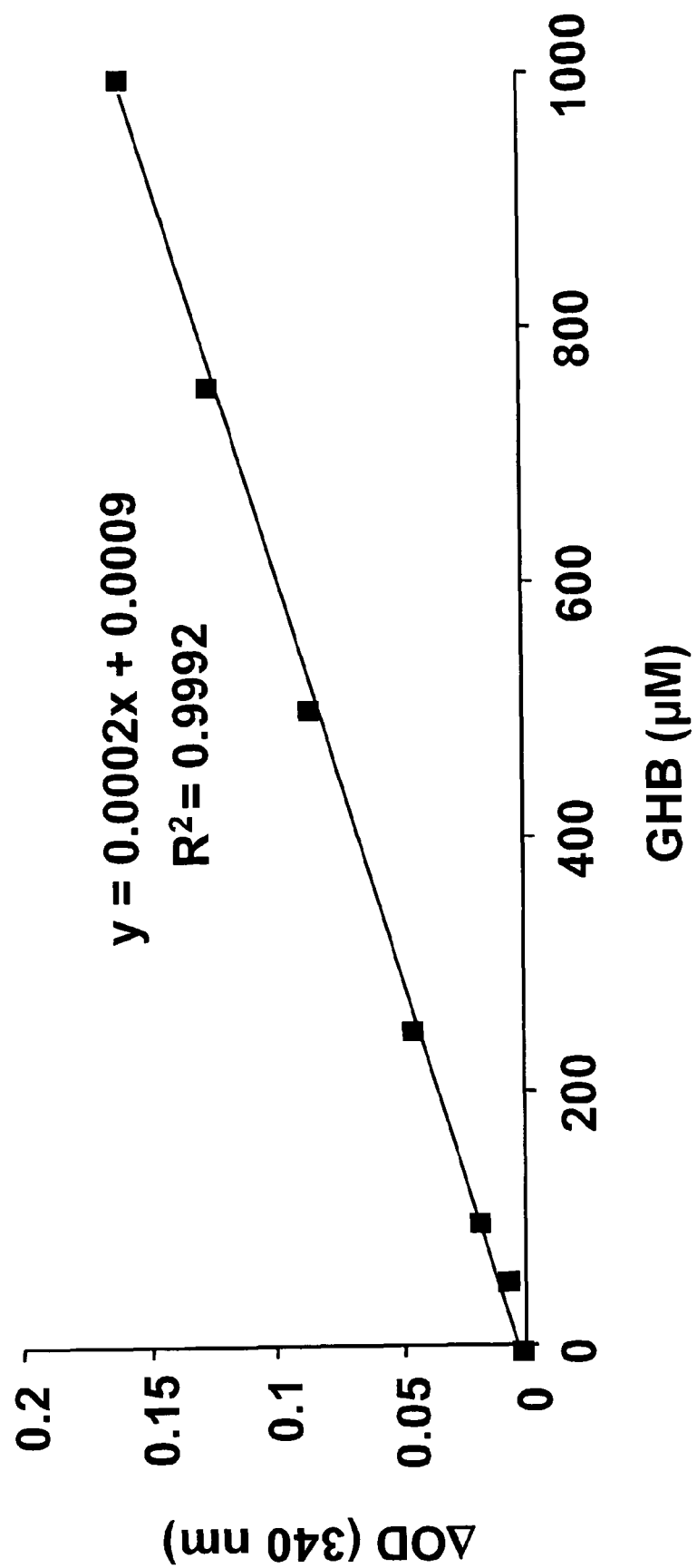
FIG. 5 shows a GHB standard curve run on a clinical chemistry analyzer (Kone T30, Thermo; two-reagent assay format; total incubation time was 8 minutes). ΔOD, difference of the optical density at 340 nm from two minutes to 8 minutes incubation time.
Figure 8:
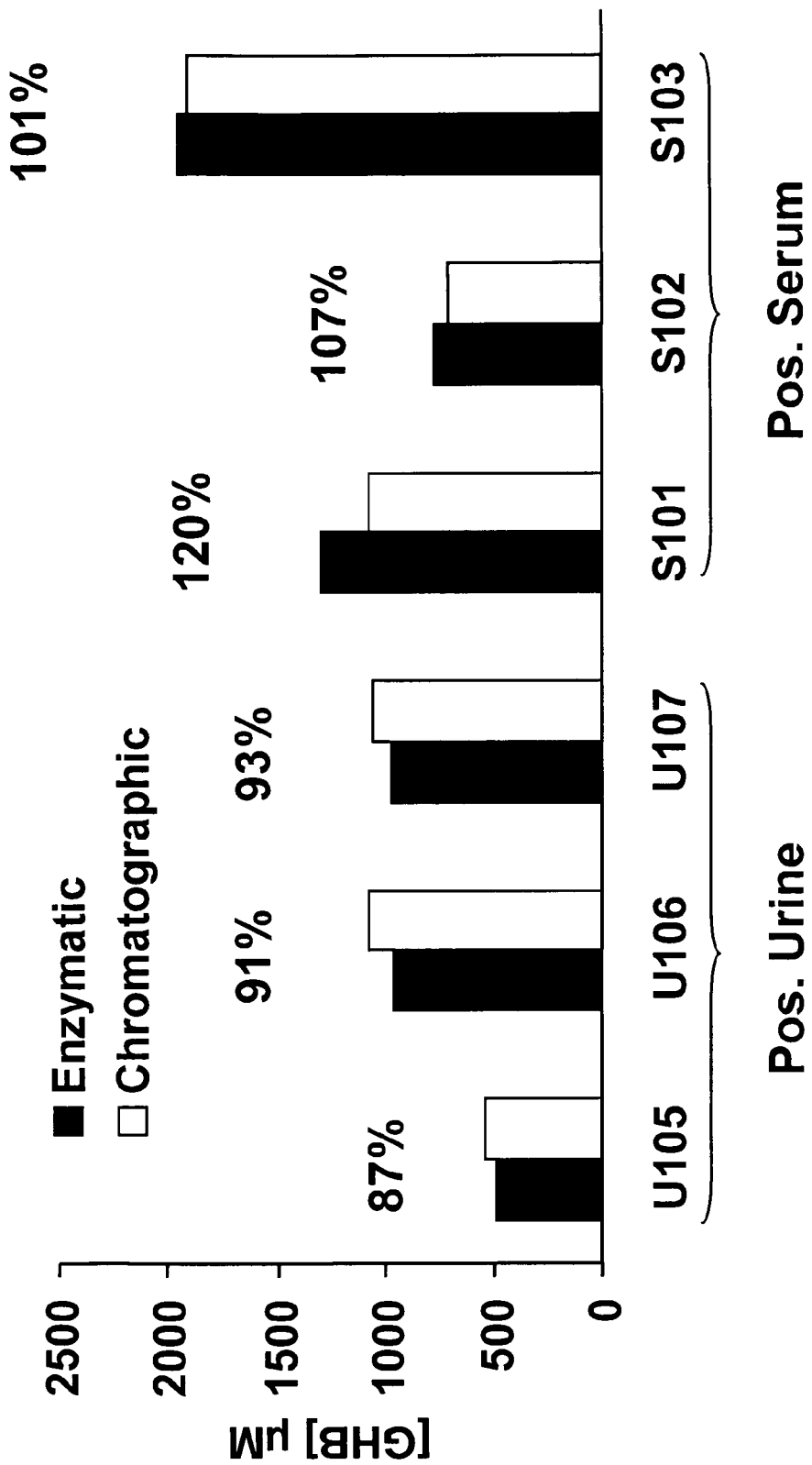
FIG. 8 shows the results of a series of assays run either on a clinical chemistry analyzer (Kone T30, Thermo; two-reagent assay format; total incubation time was 8 minutes) or in an ion chromatagraphic (IC) method to validate the accuracy of the enzymatic method of the present invention. GHB-positive serum and urine samples from intoxicated patients (n=3 each) were analyzed in the enzymatic method using the two-reagent procedure, and the results measured were compared to the results obtained with a well-established reference method based on ion chromatography (Jordi et al.: Determination of formic acid, glycolate, gamma-hydroxybutyrate together with other endogenous organic acids in human serum and urine, Diploma work at the Technical High School of both Basel, Switzerland, Departement Industry, Chemistry, Muttenz, 2003; Jordi et al.: GHB Determination with ion chromatography, Poster at the IATDMCT congress, 2003, Basel Switzerland).
Figure 9:
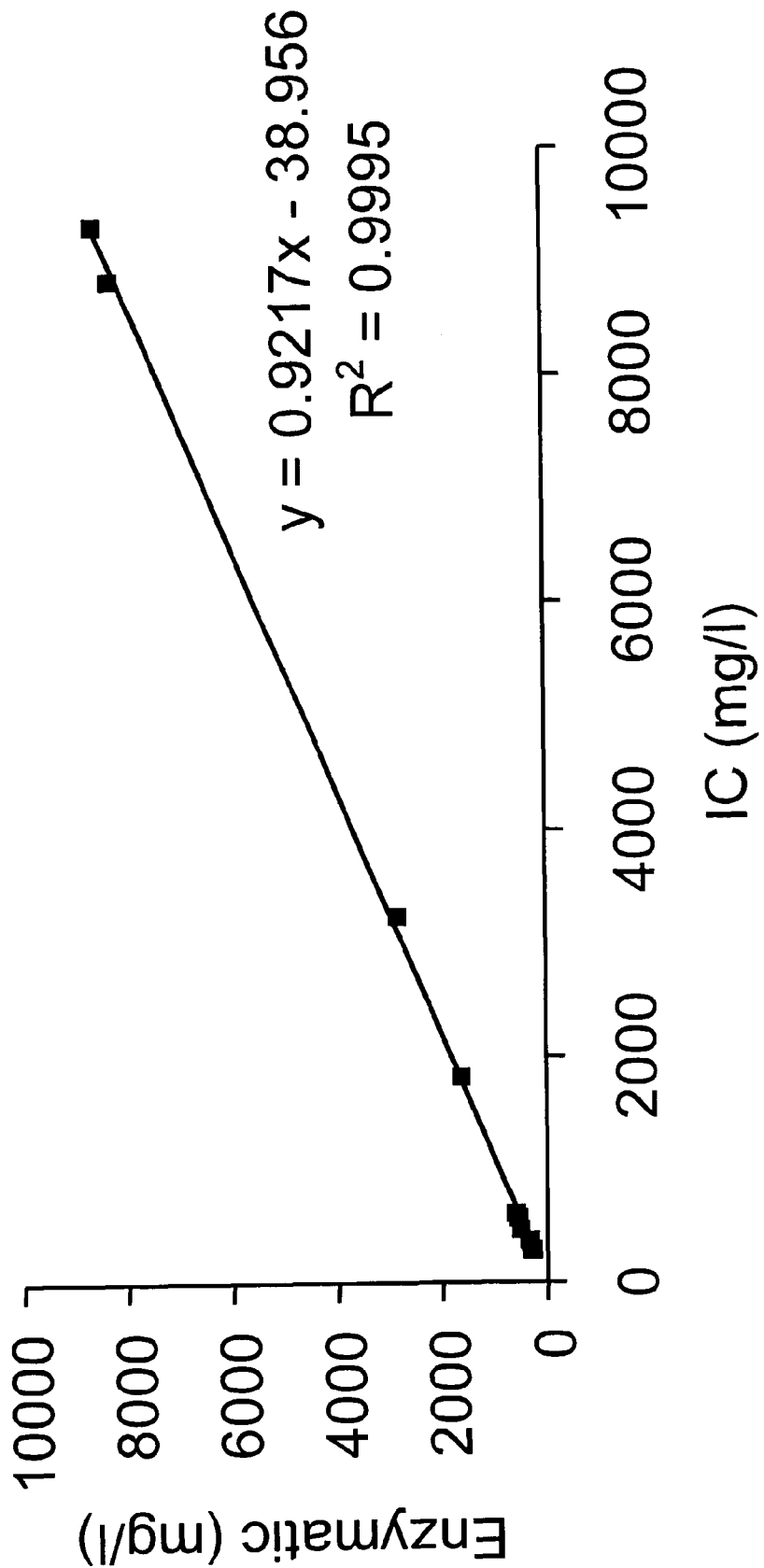
FIG. 9 shows the results of a series of assays run on a clinical chemistry analyzer (Kone T30, Thermo; two-reagent assay format; total incubation time was 8 minutes). The concentrations of GHB-positive urine samples from intoxicated patients (n=9) were determined by the enzymatic method of the present invention and correlated to the IC reference method specified in FIG. 8. Urine samples with an initial concentration above 2000 µM (~200 mg/L) were 5 to 100 times diluted with 0.9% NaCl solution and re-analyzed. GHB concentrations measured are given in mg/L.
Figure 10:
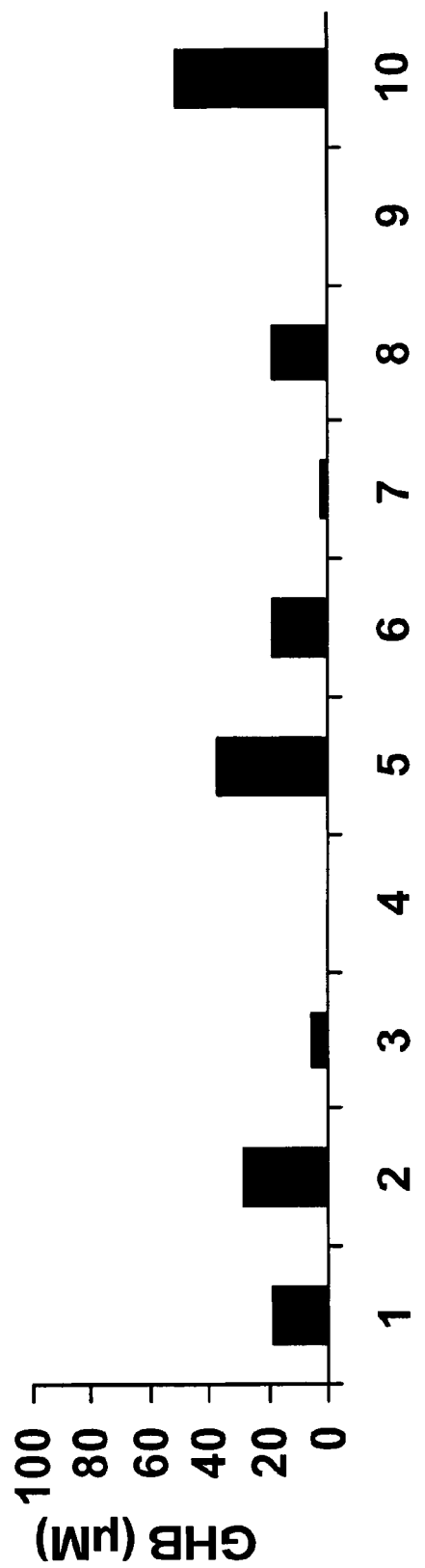
FIG. 10 shows the endogenous levels of GHB in serum and urine, respectively, of 10 normal donors each as measured with the enzymatic method of the present invention (Kone T30, Thermo; two-reagent assay format; total incubation time was 8 minutes).
Figure 10:
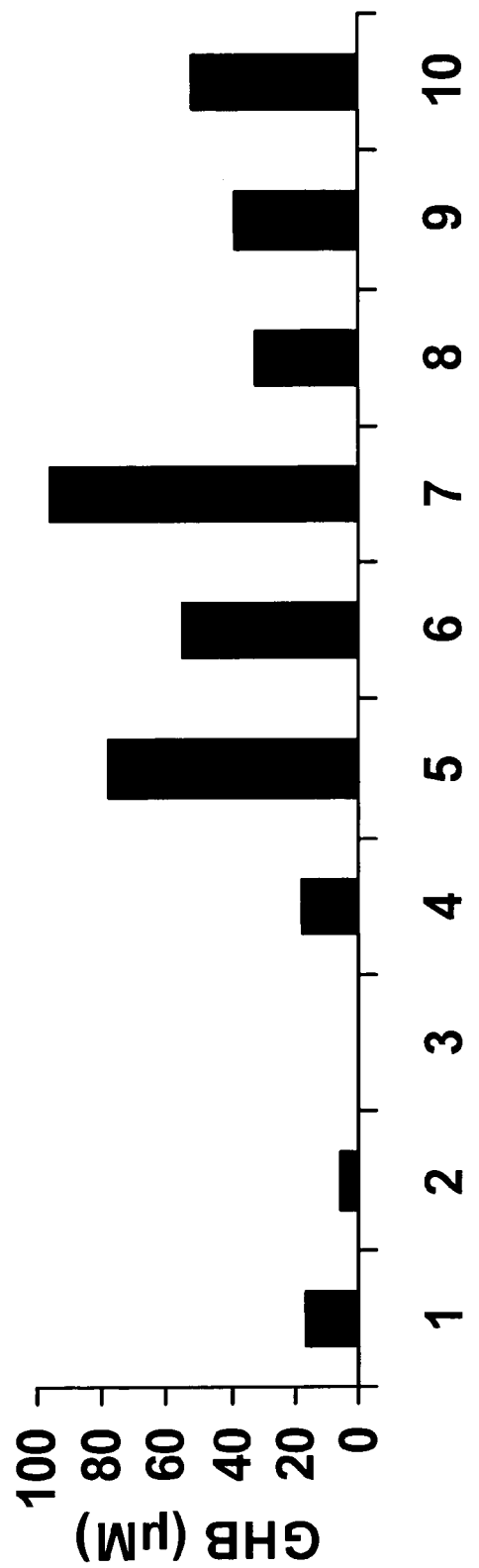

The invention claimed is:

1. A method to determine the concentration of gamma-hydroxy butyric acid (GHB) in a sample, wherein the method comprises the steps of:
    a) providing a mixture comprising an enzyme capable of converting GHB to succinic semialdehyde (SSA) by reducing an oxidized cofactor, an oxidized cofactor, wherein the oxidized cofactor is NAD+, which is reduced to NADH, the sample, a buffer, oxalic acid, and EDTA;
    b) incubating the mixture of step a);
    c) measuring the quantity of the reduced cofactor NADH in the incubated mixture obtained according to step b); and
    d) correlating the measured quantity of the reduced cofactor with the concentration of GHB in the sample.

2. The method of claim 1, wherein the enzyme of step a) is an oxidoreductase.

3. The method of claim 2, wherein the enzyme is a GHB dehydrogenase, SSA reductase, glucuronate reductase and/or an aldehyde reductase.

4. The method of claim 1, wherein the measurement of the reduced cofactor is carried out at a wavelength between 100 nm and 650 nm.

5. The method of claim 4, wherein the measurement of the reduced cofactor is carried out at a wavelength of 340 nm.

6. The method of claim 1, wherein the incubation of the mixture is carried out at a temperature of 28 to 50° C.

7. The method of claim 6, wherein the incubation of the mixture is carried out at a temperature of 37° C.

8. The method of claim 1, wherein the incubation time is between 1 and 60 minutes.

9. The method of claim 8, wherein the incubation time is 8 minutes.

10. The method of claim 1, wherein the pH value of the mixture is between 8 and 12.

11. The method of claim 10, wherein the pH value is 10.

12. The method as described in claim 1, performed at least in part with a microtiter plate.

13. The method as described in claim 1, performed at least in part with an auto-analyzer.

14. The method of claim 1, wherein the enzyme of step a) is derived from a synthetically manufactured gene construct.

15. A composition for assaying a sample for GHB, comprising the following components:
    a) an enzyme capable of converting GHB to succinic semi-aldehyde (SSA) by reducing an oxidized cofactor;
    b) an oxidized cofactor, wherein the oxidized cofactor is NAD+, which is reduced to NADH; and c) a mixture containing a buffer, oxalic acid as a glycolytic enzyme inhibitor with a concentration range between 1 and 100 mM, and EDTA with a concentration range between 0.1 and 1.5 mM.

16. The composition of claim 15, wherein the enzyme is GHB dehydrogenase.

17. The composition of claim 15, wherein the oxidized cofactor is NAD+ with a concentration range between 0.1 and 10 mM.

* * * * *